United States Patent

Rogalla et al.

[11] Patent Number: 5,835,556
[45] Date of Patent: Nov. 10, 1998

[54] PROCESS AND DEVICE FOR COMPUTER TOMOGRAPHY TRANSILLUMINATION FOR TREATMENT

[76] Inventors: Patrik Rogalla, Leberstrasse 60, D-10829 Berlin; Sven Mutze, Bradenburgische Strasse 142, D-15566 Schoneiche, both of Germany

[21] Appl. No.: 776,212
[22] PCT Filed: May 22, 1996
[86] PCT No.: PCT/DE96/00944
§ 371 Date: Mar. 26, 1997
§ 102(e) Date: Mar. 26, 1997
[87] PCT Pub. No.: WO96/37149
PCT Pub. Date: Nov. 28, 1996

[30] Foreign Application Priority Data

May 23, 1995 [DE] Germany .......................... 195 20 017.9
May 20, 1996 [DE] Germany .......................... 296 09 826 U

[51] Int. Cl.⁶ .......................................................... A61B 5/05
[52] U.S. Cl. .......................................... 378/195; 378/208
[58] Field of Search .................................. 378/208, 195, 378/197

[56] References Cited

U.S. PATENT DOCUMENTS

| D. 270,182 | 8/1983 | Wagner | D24/2 |
|---|---|---|---|
| 3,588,500 | 6/1971 | Koerner | 250/55 |
| 4,117,337 | 9/1978 | Staats | 250/491 |

(List continued on next page.)

FOREIGN PATENT DOCUMENTS

| 0562585A2 | 9/1993 | European Pat. Off. . |
|---|---|---|
| 0579036B1 | 1/1994 | European Pat. Off. . |
| 0687443A1 | 12/1995 | European Pat. Off. . |
| 0687444A2 | 12/1995 | European Pat. Off. . |
| 3609535A1 | 9/1987 | Germany . |
| 3808009C2 | 9/1988 | Germany . |
| 3937077C2 | 5/1989 | Germany . |
| 4202302A1 | 7/1993 | Germany . |
| 4218637C1 | 11/1993 | Germany . |
| 92183220 | 1/1994 | Germany . |
| WO93/22969 | 11/1993 | WIPO . |
| WO96/37149 | 11/1996 | WIPO . |

OTHER PUBLICATIONS

Rofo–Fortschr–Geb–Röntgenstr–Neuen–Bildgeb–Verfahr. 1992 Jul., 157(1), 29–33; Klose, K. C. et al.: "Percutaneous CT–controlled cutting–needle biopsy of diffuse interstitial and alveolar lung diseases–the technic and results".

AJR–Am–J–Roentgeonol. 1993 Aug., 161(2), 273–8; Yankelevitz, D. F. et al.: "Percutaneous CT biopsy of chest lesions: an in vitro analysis of the effect of partial volume averaging on needle positioning".

Radiology 1994 Jan., 190(1), 243–6; Sakai, T. et al. "CT–guided biopsy of the chest: usfulness of fine–needle core biopsy combinde with frozen–section pathologic diagnosis".

Abdom–Imaging 1994 May–Jun., 19(3), 217–20; Hussain, S. et al.: "Dual–angled CT–guided biopsy".

(List continued on next page.)

Primary Examiner—Don Wong
Attorney, Agent, or Firm—Birch, Stewart, Kolasch & Birch, LLP

[57] ABSTRACT

A computed tomography-fluoroscopy method is invented for interventions comprising the steps of combining a floating patient table with a cross-sectional imaging modality for interventions under visual computed tomography control. A handle is installed on the patient table, which is mechanically decoupled from the central control system. During an intervention, the table is brought to a random position, and a single-scan or scan-series is triggered. A light-beam localizer is used for orientation and positioning the single-scan or scan-series.

7 Claims, 1 Drawing Sheet

U.S. PATENT DOCUMENTS

| | | | |
|---|---|---|---|
| 4,145,612 | 3/1979 | Cooper | 378/208 |
| 4,233,507 | 11/1980 | Volz | 250/252 |
| 4,360,028 | 11/1982 | Barbier et al. | 128/659 |
| 4,538,289 | 8/1985 | Scheibengraber | 378/20 |
| 4,608,977 | 9/1986 | Brown | 128/303 |
| 4,870,666 | 9/1989 | Lonn et al. | 378/18 |
| 4,907,251 | 3/1990 | Mork et al. | 378/39 |
| 4,914,682 | 4/1990 | Blumenthal | 378/20 |
| 4,947,418 | 8/1990 | Barr et al. | 378/208 |
| 5,093,852 | 3/1992 | Nishikawa et al. | 378/39 |
| 5,199,060 | 3/1993 | Kato | 378/196 |
| 5,243,639 | 9/1993 | Johnson | 378/208 |
| 5,255,303 | 10/1993 | DiMaio et al. | 378/208 |
| 5,373,543 | 12/1994 | Ackermann et al. | 378/20 |
| 5,411,026 | 5/1995 | Carol | 128/660 |
| 5,447,154 | 9/1995 | Cinquin et al. | 128/653.1 |
| 5,485,839 | 1/1996 | Swerdloff | 378/4 |
| 5,598,269 | 1/1997 | Kitaevich et al. | 378/208 |
| 5,628,327 | 5/1997 | Grönemayer et al. | 378/20 |
| 5,638,416 | 6/1997 | Ingwersen | 378/4 |
| 5,640,436 | 6/1997 | Kawai et al. | 378/4 |
| 5,661,773 | 8/1997 | Swerdloff et al. | 378/65 |
| 5,690,107 | 11/1997 | Hofmann | 128/653.1 |

OTHER PUBLICATIONS

Nucl–Med–Biol. 1994 Jul., 21(5), 713–9; Belfiore, G. et al.: "CT–guided biopsy of lung lesions".

Radiol. 1995 Apr., 76(4), 201–4; Guessous, K. et al. "Failure factors in X–ray computed tomography–guided biopsy of pulmonary lesions: analysis of 103 consecutive biopsies".

J–Compute–Assist–Tomogr. 1995 May–Jun., 19(3), 434–9; Mody, M. K. et al.: "Percutaneous CT–guided biopsy of adrenal masses: immediate and delayed complications".

81st scientific assembly of the RSNA, Chicago, 1995 Dec.; Rogalla et al. : "CT fluoroscopy for lung biopsies: new low–risk and time–saving technique".

Eur–Radiol. 1996, 6(4), 420–4; Sartoris, F. et al.: "CT–guided needle localization of lung nodules for thoracoscopic resection".

Radiology 1996 Sep., 200(3), 851–6; Katada, K. et al.: "Guidance with real–time CT fluoroscopy: early clinical experience".

Radiology 1996 Nov., 201(2), 576–8; Kato, R. et al.: "Radiation dosimetry at CT fluoroscopy: physican's hand dose and development of needle holders".

82st scientific assembly of the RSNA, Chicago, 1996 Dec.; Templeton, P. A. et al.: "Real–time continuous imaging CT guidance for lung biopsies".

AJR–Am–J–Roentgenol. 1997 Aug., 169(2), 393–4; White, C. S. et al.: "CT–assistd transbronchial needle aspiration: usefulness of CT fluoroscopy".

83st scientific assembly of the RSNA, Chicago, 1997 Dec.; Templeton, P. A. et al. : "Lung nodules 1.5 cm or smaller in size: CT biopsy success using CT fluoroscopy".

PROCESS AND DEVICE FOR COMPUTER TOMOGRAPHY TRANSILLUMINATION FOR TREATMENT

FIELD OF THE INVENTION

The invention relates to a method and an apparatus on scannographs, in particular for computed tomographyradioscopy for interventions, and refers to adjustment of a table for the patient, fixing of its position, as well as triggering of a light-beam localiser and of a single scan after mechanical decoupling of the scannograph from the central control system.

DESCRIPTION OF THE BACKGROUND ART

Computed tomography has enriched medical diagnostics in an extraordinary manner and not only rendered numerous radiation-exposing X-ray examinations, such as encephalography or angiography, superfluous but also took advantage of the tomograms gained thereby for planning and checking the radiation therapy of tumors. Numerous pathological processes in the entire trunk of the body, such as carcinomata or enlarged lymph nodes, can be classified only by withdrawal of tissue and subsequently treated. Such biopsies can, inter alia, be carried out with the help of computed tomography. When doing so, the position of a needle introduced into the body is represented by executing a single sectional drawing in the plane of the needle.

After corresponding preparation of the patient, i.e. after positioning of said patient and disinfection of the skin of same as well as after having locally anaesthetised the point of puncturing, the biopsy needle is, usually outside the gantry, introduced so as to lie under the surface of the skin and, thereafter, the table with the patient will be moved into the gantry for conduction of the first check scan. Control of that procedure is effected from the console of the scannograph, which console, for reasons of radiation protection, is situated outside the examination room. When a lamination is radiographed, the medical personnel are not in the examination room. After the sectional drawing has been displayed on the monitor, the patient is moved out of the gantry. After a possibly required positional correction of the needle, another radiograph is taken once the table with the patient has been moved into the gantry through the console. The entire procedure—moving of the patient out of the gantry and into the gantry again—takes up a great deal of time and, during the whole examination, the patient must remain quiet and motionless.

Various solutions have been proposed, dealing with positioning of the patient resp of specific parts of the body or of tables for patients as exactly as possible, e. g.:

- positioning of a patient, in case of a medical panoramic radiographic facility, with the help of a sensor for determining the relative position of an object to be examined towards the radiographic facility, the determined data being compared with those of the relative position of a tomographic zone towards the radiographic facility (German Patent resp Laying-open Specification 38 08 009),
- a fixed device for holding the patient whereas the housing of the scannograph can be linearly displaceably) guided by means of driving and guiding facilities (German Utility Model 92 18 322),
- a motor-driven and computer-controlled day-bed for the patient, which day-bed can be moved into the housing of the scannograph,
- moving the patient synchronously with radiographing successive scans, departing from an initial position—e.g. in case of examinations of the area of the cranium (European Patent 579 036),
- a scannograph housing for receiving the day-bed with the patient, in which case—in order to avoid information losses between diagnosis and surgical treatment—the day-bed for the patient is, at the same time, constructed as an operating table (German Patent resp Laying-open Specification 42 02 302),
- physicians' or dentists' examination facilities, e.g. for radiographing the temporomandibular joint (German Patent resp Laying-open Specification 39 37 077) or for scannographing the knee after fixation of the lower leg (German Patent resp Laying-open Specification 38 09 535),
- scannograph with means for generating a silhouette which is represented on a monitor synchronously with the respective position of the measuring system towards the day-bed for the patient (German Patent 42 18 637, U.S. Pat. No. 5,373,543).

DETAILED DESCRIPTION OF THE PREFERRED EMBODIMENTS

Figure 1:
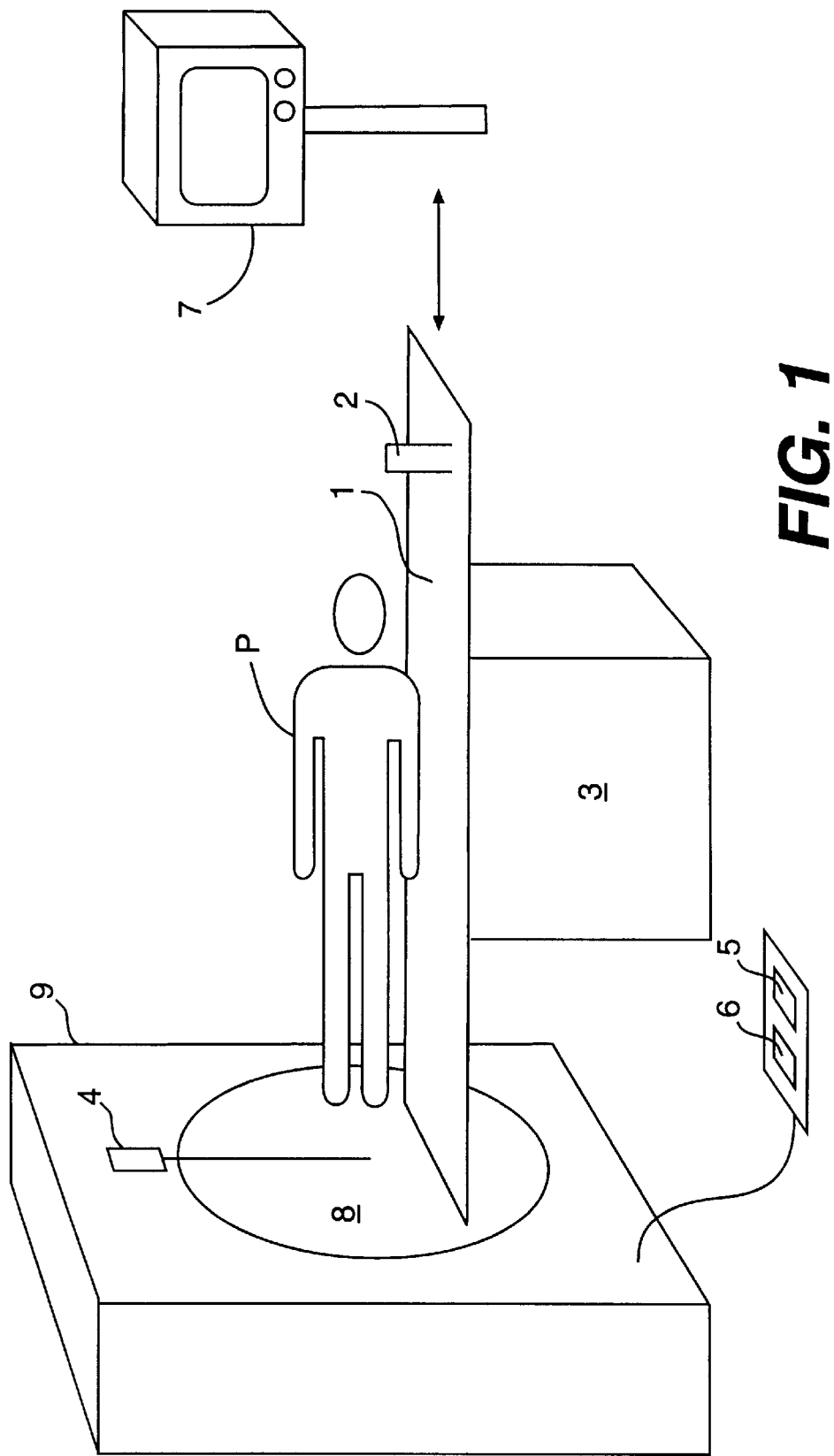

The invention is based on the object to develop a method and an apparatus by which, for computed tomography-radioscopy for interventions, exact positioning of the patient can be achieved and the number of scans for seeking the needle can be reduced.

This object was solved by combining a floating table for the patient with a sectional drawing modality for biopsies under a visual ct check. The apparatus according to the invention comprises a table for the patient, which is included in a scannograph and which is provided with a handle serving for mechanically setting a random position of the table after decoupling from the central control system, and foot switches for triggering a light-beam localiser on the one hand and a single scan on the other hand. The handle newly mounted to the table for the patient enables random positioning of the table after mechanical decoupling from central control. The foot switches are installed in the examination room. They can trigger both the light-beam localiser and a single scan.

The term "floating table for the patient" designates a day-bed for the patient, which, with but small mechanical effort, can freely be moved by the examining person along an axis at any time during examination.

By "sectional drawing modality" an examination technique is meant which, for visualising an examined object, generates sectional drawings in a plane with a defined lamination thickness. The sectional drawing modalities include computed tomography, ultrasonics or nuclear spin resonance tomography.

Installation of the handle on the table for the patient enables setting of any table position by hand during surgical treatment. The digitally indicated table position always corresponds to the real position. The light-beam localiser is triggered via an additionally installed foot switch in the examination room just like—via a further foot switch a single scan (one lamination). In order to check the position of the needle, the table is—without any control from the console—rapidly moved out of the gantry and into the gantry again so that a fresh single scan can be triggered.

Surprisingly, it was found that the way of proceeding according to the invention provides, considering all the modifications—light, single scan following a pressure exerted by the foot, manually movable table with position indicator, and immediate tomogram monitoring, an examination modality by which biopsies can be conducted in more reliable a manner and which will lead to shortened examination periods. Since the patient can, by hand, be rapidly moved out of the gantry and into the gantry again—without having to leave the examination program—, the required amount of time will be considerably reduced. In order that the physician may stay in the room for inspecting the tomogram—, the latter as taken becomes visible to the examining person on a monitor standing in the gantry room.

Another advantage resides in that the patient is less exposed to radiation since, due to the exact table position achieved in accordance with the invention, superfluous scans for seeking the needle will be avoided. During surgical treatment, the medical personnel will remain in the examination room so as to affect the psyche of the patient in positive manner, if need be.

Apart from saving time, application of the method and apparatus according to the invention brings about multiplication of the technical possibilities and shows another new way in the field of computed tomography-radioscopy for interventions. Further advantages reside in minor exposition to radiation due to reduction of superfluous scans, in higher sensitivity, and, indirectly, in less complications as well—primarily due to the fact that the frequent manipulation, in case of needle correction, is not required any more under computed tomography-radioscopy.

With conventional radioscopy, continuous projection roentgenograms are produced, not permitting any spatial allocation. When doing so, a needle is guided to its destination under constant irradiation insofar as said destination can be made out at all in the projection. The hand of the examining person is mainly situated in the direct optical path.

However, movement of the table for the patient—which, on principle, is possible with most X-ray apparatuses—will not be brought about since puncturing is carried out under X-ray vision and the represented roentgenogram depicts areas of from 5 by 5 to 35 by 35 cm. Insofar, the invention is based on a principle which is different from single-scan triggering and moving the table by hand.

A manually operated scannograph has not become known since such a scannograph, because of the usually required lamination examination at defined lamination distances, cannot be realised and is of no clinical relevance. The combination of a floating table with a sectional drawing modality is new. Moreover, it would make sense only for biopsies under a visual ct check.

The invention shall be explained in detail on the basis of one embodiment.

Embodiment

The table 1 for the patient P is equipped with a handle 2 enabling the table to be taken to a random position after mechanical decoupling from central control 3. The digital indication of the table position is not affected thereby. After the patient P has been prepared in the usual way, the physician, subsequently to switching on of the light-beam localiser 4 via an additionally installed foot switch, 5 can now exactly position the table 1 within the sectional drawing modality 9. Then, a single scan (one lamination) will be triggered in the examination room via a second foot switch 6. Four seconds later, the tomogram will appear on a monitor 7; it will appear after one second, provided that all additional filters and subsequent tomogram processings are done without. The tonogram as taken becomes visible to the examining person on a monitor 7 standing in the gantry room.

The physician will remain in the examination room and, during surgical treatment, can affect the psyche of the patient P in positive manner. When the position of the needle has to be checked, the table 1 can rapidly be moved out of the gantry 8 and into the gantry 8 again without any control from the console. Thereafter, a fresh single scan can be triggered. The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A computed tomography-radioscopy method for intervention comprising the steps of:

providing a floating table for a patient;

providing a sectional drawing modality for biopsies under a visual computed tomography check;

providing a monitor;

manually moving the floating table for a patient;

electronically monitoring a table position of the floating table for the patient; and displaying the table position relative to the sectional drawing modality on the monitor.

2. The method according to claim 1, further comprising the steps of:

providing a handle on the floating table for a patient;

providing a central control system;

decoupling the floating table for a patient from the central control system prior to said step of manually moving the floating table for a patient; and using the handle during said step of manually moving the floating table for a patient.

3. A computed tomography-radioscopy apparatus for interventions comprising:

a floating table for a patient;

a gantry for receiving said floating table for a patient;

a sectional drawing modality for biopsies under a visual computed tomography check located within said gantry;

a monitor located adjacent said gantry;

electronic circuitry attaching said monitor to said floating table for a patient, said electronic circuitry causing said monitor to display a table position of said floating table for a patient relative to said sectional drawing modality; and a handle attached to said floating table for a patient for allowing an operator to manually move said floating table for a patient.

4. The apparatus according to claim 3, further comprising:

means for decoupling the floating table for a patient from a central control system, an operator being allowed to manually move said floating table for a patient only after said means for decoupling has decoupled said floating table from said central system; and a switch for triggering at least one of a light-beam localizer and a single scan.

5. The apparatus according to claim 4, wherein said switch comprises at least one foot switch.

6. The apparatus according to claim 4, wherein said monitor also allows an operator to see a taken tomogram.

7. The apparatus according to claim 3, wherein said monitor also allows an operator to see a taken tomogram.

* * * * *